(12) United States Patent
Fritsch

(10) Patent No.: US 11,213,431 B2
(45) Date of Patent: Jan. 4, 2022

(54) NITINOL TYMPANOSTOMY TUBE

(71) Applicant: Ear Tech, LLC, Indianapolis, IN (US)

(72) Inventor: Michael H. Fritsch, Indianapolis, IN (US)

(73) Assignee: Ear Tech, LLC, Indianapolis, IN (US)

( * ) Notice: Subject to any disclaimer, the term of this patent is extended or adjusted under 35 U.S.C. 154(b) by 167 days.

(21) Appl. No.: 16/267,729

(22) Filed: Feb. 5, 2019

(65) Prior Publication Data

US 2019/0167481 A1 Jun. 6, 2019

Related U.S. Application Data

(60) Continuation of application No. 15/161,379, filed on May 23, 2016, now Pat. No. 9,987,168, which is a division of application No. 13/764,875, filed on Feb. 12, 2013, now Pat. No. 9,907,699.

(60) Provisional application No. 62/628,051, filed on Feb. 8, 2018, provisional application No. 61/668,407, filed on Jul. 5, 2012.

(51) Int. Cl.
*A61F 11/00* (2006.01)

(52) U.S. Cl.
CPC ............ *A61F 11/002* (2013.01); *A61F 11/00* (2013.01)

(58) Field of Classification Search
CPC ............ A61F 11/002; A61F 2250/0039; A61F 2250/001; A61F 2250/0082; A61F 2002/183; A61F 2002/086; A61F 2210/0076; A61F 2210/0004; A61F 2210/0061; A61F 2/06; A61F 2/18; A61F 2/07; A61F 11/00; A61F 2230/0006; A61F 2230/0063; A61F 2230/0069; A61F 2230/005; A61M 2210/0662; A61M 31/00; A61M 25/01; A61M 25/0662; A61M 27/00; A61M 27/006; A61M 2025/0025; A61B 2017/00787; A61B 17/3468; A61B 1/227
See application file for complete search history.

(56) References Cited

U.S. PATENT DOCUMENTS

| | | |
|---|---|---|
| 3,601,128 A | 8/1971 | Hakim |
| 5,282,847 A | 2/1994 | Trescony et al. |
| 2007/0207186 A1* | 9/2007 | Scanlon .................... A61F 2/91 424/424 |

(Continued)

FOREIGN PATENT DOCUMENTS

DE 102012218164 A1 6/2014

*Primary Examiner* — Mohamed G Gabr
(74) *Attorney, Agent, or Firm* — Indiano Law Group LLC; E. Victor Indiano; John T. Woods, III

(57) ABSTRACT

A tympanostomy tube includes a nitinol body having a first configuration and a second configuration. In the first configuration, the nitinol body has a first cylindrical shape defining a first end, a central region, a second end, a longitudinal axis, and a lumen extending longitudinally through the nitinol body. In the second configuration, the nitinol body is expanded and has a second cylindrical shape different than the first cylindrical shape and defines the first end, the central region, the second end, the longitudinal axis, and the lumen. A diameter of the lumen at one of the first end, the central region, and the second end is larger in the second configuration than the diameter of the lumen at the corresponding first end, central region, or second end in the first configuration.

17 Claims, 10 Drawing Sheets

(56) References Cited

U.S. PATENT DOCUMENTS

| | | | |
|---|---|---|---|
| 2008/0058831 A1* | 3/2008 | Fujiwara | A61F 11/002 606/109 |
| 2008/0262468 A1 | 10/2008 | Clifford et al. | |
| 2009/0209972 A1* | 8/2009 | Loushin | A61F 11/002 606/109 |
| 2014/0094733 A1* | 4/2014 | Clopp | A61M 27/002 604/8 |
| 2015/0290040 A1* | 10/2015 | Vaughan | A61F 11/002 606/109 |
| 2017/0048628 A1* | 2/2017 | McElveen | A61F 2/18 |
| 2017/0319390 A1 | 11/2017 | Skovlund | |

* cited by examiner

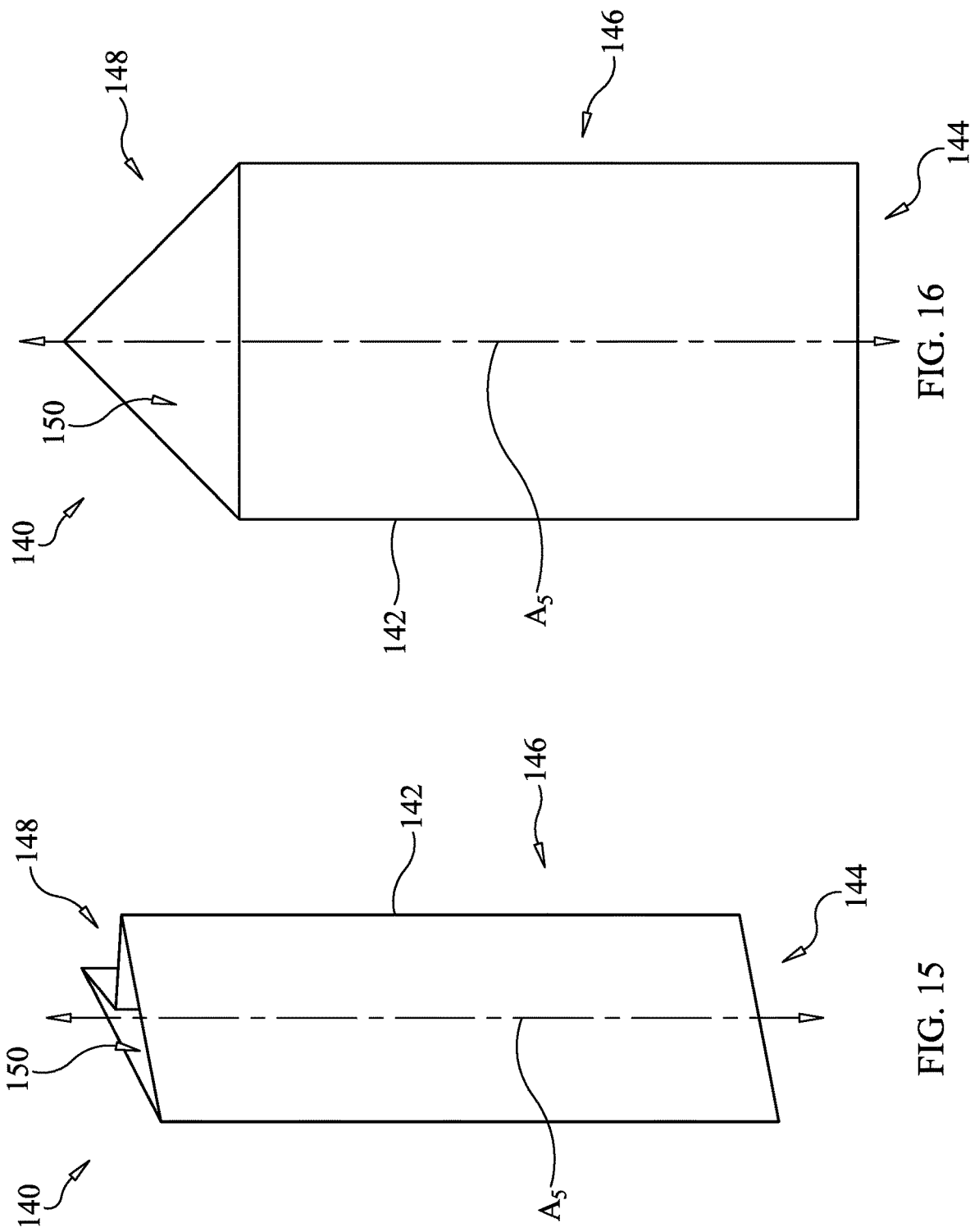

NITINOL TYMPANOSTOMY TUBE

CROSS-REFERENCE TO RELATED APPLICATIONS

This application claims the benefit of U.S. Provisional Patent Application No. 62/628,051, filed Feb. 8, 2018. The present application is a continuation-in-part of pending U.S. patent application Ser. No. 15/161,379, for a ONE-STEP TYMPANOSTOMY TUBE AND METHOD FOR INSERTING SAME, which was filed on 23 May 2016; which is a divisional application of pending U.S. patent application Ser. No. 13/764,875, for a ONE-STEP TYMPANOSTOMY TUBE AND METHOD FOR INSERTING SAME, which was filed on 12 Feb. 2013, and which claims benefit of priority to U.S. Provisional Patent Application No. 61/668,407, that was filed on 5 Jul. 2012; all of which are fully incorporated herein by reference.

TECHNICAL FIELD

The present disclosure relates generally to tympanostomy tubes and, more particularly, to a nitinol metal alloy tympanostomy tube.

BACKGROUND

A tympanostomy tube is a small tube inserted into the tympanic membrane in order to ventilate the middle ear for a prolonged period of time, and to prevent the accumulation of fluid in the middle ear. The tube may be inserted under general anesthesia or local anesthesia. To perform the procedure, a surgeon may use a myringotomy knife to make an incision in the tympanic membrane. Then, the surgeon may use forceps, a probe, and/or other device to insert the tympanostomy tube.

SUMMARY OF THE INVENTION

In one aspect, a tympanostomy tube includes a nitinol body having a first configuration and a second configuration. In the first configuration, the nitinol body has a first geometric shape defining a first end, a central region, a second end, a longitudinal axis, and a lumen extending longitudinally through the nitinol body. In the second configuration, the nitinol body has a second geometric shape different than the first geometric shape and defines the first end, the central region, the second end, the longitudinal axis, and the lumen.

In another aspect, a method for inserting a tympanostomy tube having a nitinol body is provided. The method includes a step of providing the tympanostomy tube in a first configuration in which the nitinol body has a first cylindrical shape defining a first end, a central region, a second end, a longitudinal axis, and a lumen extending longitudinally through the nitinol body. The method, thereafter, includes inserting the tympanostomy tube through a tympanic membrane. After the inserting step, the tympanostomy tube is transformed from the first configuration to a second configuration in which the nitinol body has a second cylindrical shape different than the first cylindrical shape and defines the first end, the second end, the central region, the second end, the longitudinal axis, and the lumen. A diameter of the lumen at one of the first end, the central region, and the second end is larger in the second configuration than the diameter of the lumen at the corresponding first end, central region, or second end in the first configuration.

Other features and aspects will be apparent from the following description and accompanying drawings.

BRIEF DESCRIPTION OF THE DRAWINGS

FIG. 15 is a side view of yet another exemplary embodiment of a tympanostomy tub, show in a first configuration, according to the present disclosure;

FIG. 16 is a side view of the tympanostomy tube of FIG. 15, shown in a second configuration, according to the present disclosure.

DETAILED DESCRIPTION

Figure 2:
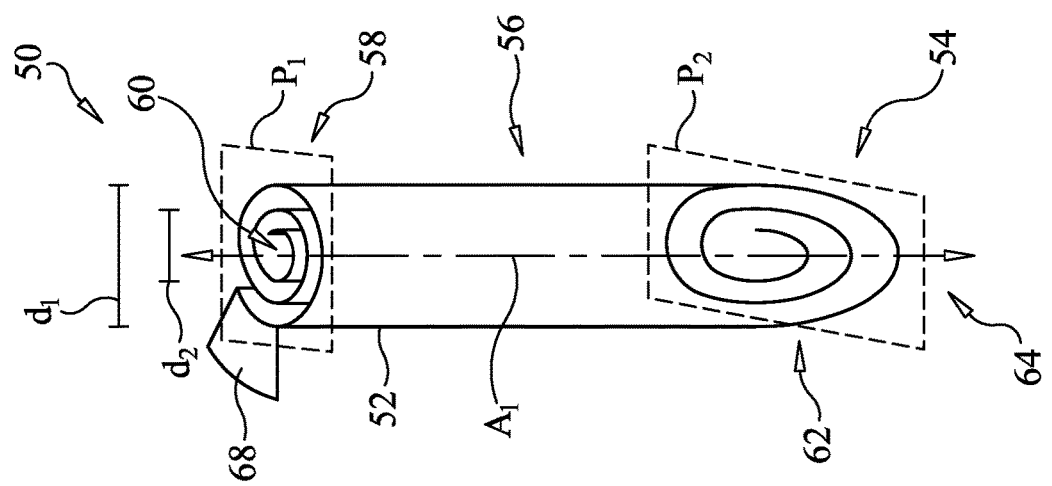
FIG. 2 is a side view of an exemplary embodiment of a tympanostomy tube, shown in a first configuration, according to the present disclosure.

Reference will now be made in detail to specific embodiments or features, examples of which are illustrated in the accompanying drawings. Wherever possible, corresponding or similar reference numerals will be used throughout the disclosure and accompanying drawings to refer to the same or corresponding parts.

Figure 1:
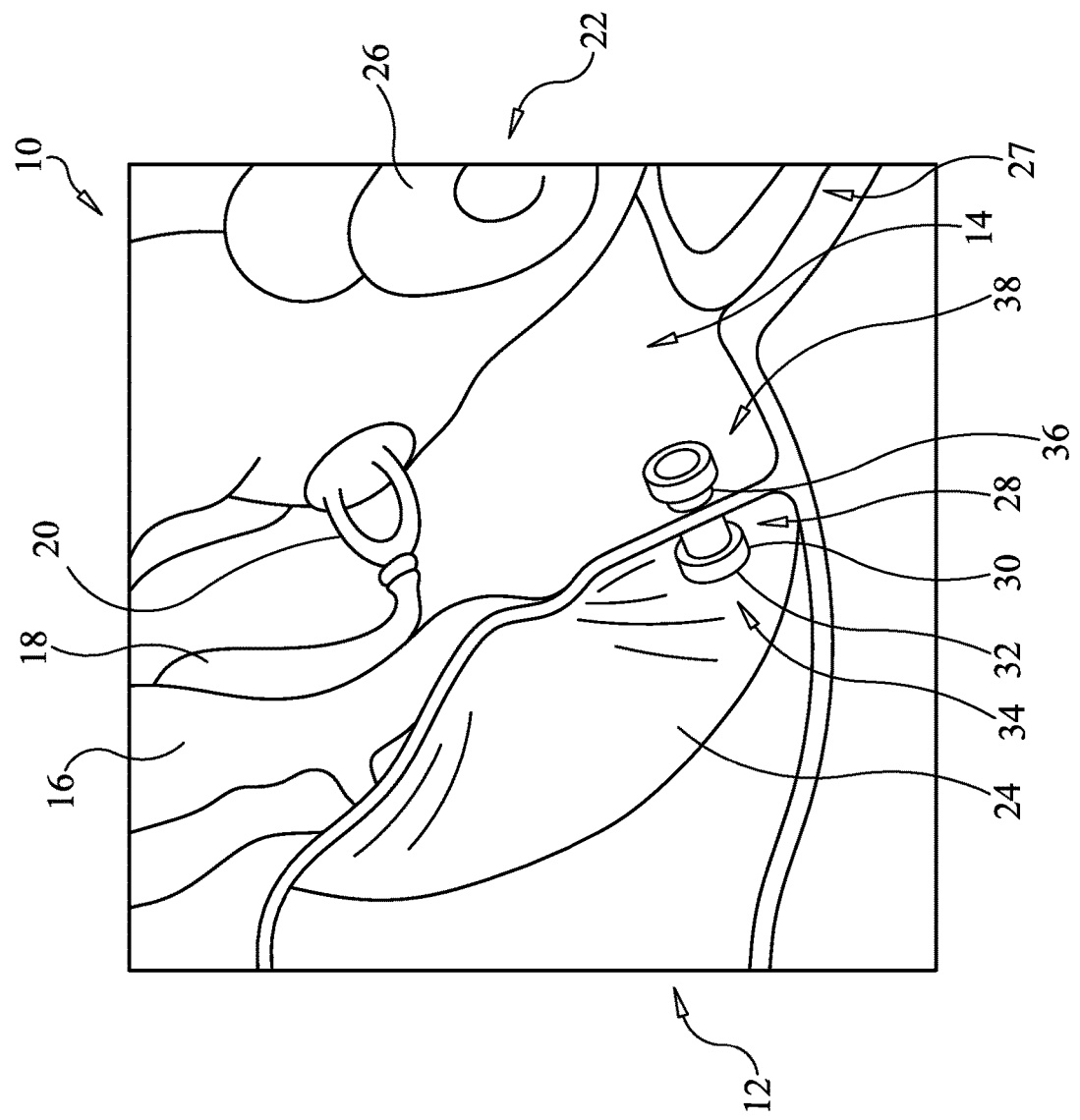
FIG. 1 is a side view of a prior art tympanostomy tube inserted in an ear canal, according to the present disclosure.

FIG. 1 illustrates a portion of an ear 10, including parts of the ear 10 relevant to the present disclosure. For example, the ear 10 includes an outer ear portion 12 and a middle ear portion 14, which includes the malleus 16, incus 18, and stapes 20. The malleus 16, incus 18, and stapes 20 are small bones that are connected and transmit sound waves to an inner ear portion 22. A tympanic membrane 24, also referred to as the eardrum, separates the outer ear portion 12 from the middle ear portion 14. The inner ear portion 22 includes the cochlea 26, vestibule (not shown), and semicircular canals (not shown), which together function to provide hearing and balance. The eustachian tube is shown at 27.

Also depicted in FIG. 1 is an exemplary prior art tympanostomy tube 28 placed in the tympanic membrane 24 in order to ventilate the middle ear portion 14. The prior art tympanostomy tube 28 is shaped like a grommet, having a tubular body 30 with a flange 32, or collar, at a first end 34 and a flange 36, or collar, at a second end 38. This type of tympanostomy tube 28 is typically intended for shorter term use, while a T-shaped tympanostomy tube (not shown) is typically intended for longer term use. The T-shaped tympanostomy tube generally includes a tubular body having a pair of longer arms extending radially therefrom, which are positioned in the middle ear portion 14 of the ear 10. The longer arms prevent natural body extrusion of the T-shaped tympanostomy tube from the eardrum.

Turning now to FIG. 2, a first exemplary embodiment of a tympanostomy tube 50, according to the present disclosure, is shown. The tympanostomy tube 50 generally includes a nitinol body, such as a nitinol foil, 52 having a first configuration and a second configuration. The nitinol body/foil 52 may define the body of the tympanostomy tube 50 and may be made from a thin sheet of nickel titanium alloy, also referred to as nitinol, or other shape memory material such as, for example, a polymer, ceramic, or alloy. Additionally and/or alternatively, the nitinol body 52 may be made using a mesh foil with perforations, such that cells could grow into the tympanostomy tube 50 and assist in stabilizing the tympanostomy tube 50.

In the first configuration, the nitinol body/foil 52 is scrolled and has a first cylindrical, or other geometric, shape, as shown. The nitinol body/foil 52, according to the first configuration, defines a first end 54, a central region 56, a second end 58, a longitudinal axis $A_1$, and a lumen 60 extending longitudinally through the nitinol body/foil 52. When placed in the ear 10 of FIG. 1, the first end 54 may be positioned in the middle ear portion 14, the central region 56 may be positioned through the tympanic membrane 24, and the second end 58 may be positioned within the outer ear portion 12. The lumen 60, which is substantially parallel to the longitudinal axis $A_1$, provides ventilation of the middle ear portion 14.

The second end 58 may terminate in edges lying in a plane $P_1$ substantially perpendicular to the longitudinal axis $A_1$. The first end 54 may terminate in edges that lie in a different plane $P_2$ that is angled relative to the longitudinal axis $A_1$, thus defining a bevel 62. The first end 54, or bevel 62 thereof, may define a beveled scroll 64 useful in piercing or cutting the tympanic membrane 24 during insertion of the tympanostomy tube 50.

Figure 3:
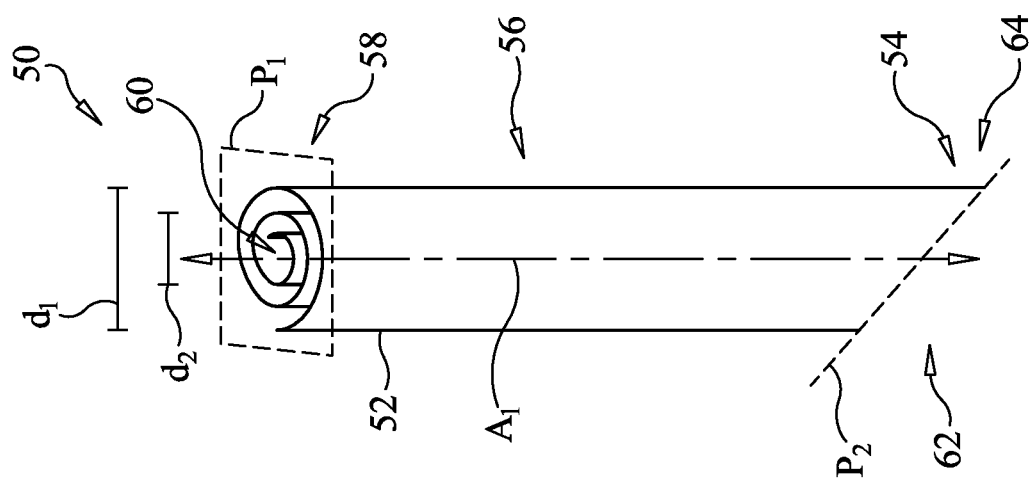
FIG. 3 is another side view of the exemplary tympanostomy tube of FIG. 2, shown in the first configuration, according to the present disclosure.

According to the first configuration of this embodiment, the nitinol body/foil 52 may be scrolled such that an outer diameter $d_1$, shown in FIG. 3, is suitable for insertion of the tympanostomy tube 50 through the tympanic membrane 24. Due to the scrolled configuration of the nitinol body/foil 52, an inner diameter $d_2$ of the nitinol body/foil 52 may be relatively reduced.

The tympanostomy tube 50 may be formed according to the first configuration with the nitinol body/foil 52 at a first temperature. When the tympanostomy tube 50 is heated above its transformation temperature, it will transform according to the second configuration, shown in FIG. 4. According to the second configuration, the nitinol body/foil 52 is un-scrolled and has a second cylindrical, or other geometric, shape different than the first cylindrical shape. In particular, the outer diameter $d_1$ and the inner diameter $d_2$ may both increase in the second configuration relative to the first configuration. The nitinol body/foil 52 may be un-scrolled such that there is little or no circumferential overlap, as shown.

Edge, or edges, defining the second end 58 may continue to lie in the perpendicular plane $P_1$ in the first configuration; however, an edge, or edges, defining the first end 54 may un-scroll, or expand, to define uneven flaps 66 extending longitudinally from the central region 56. Transformation of the tympanostomy tube 50 from the first configuration, of FIGS. 2 and 3, to the second configuration, of FIG. 4, may occur during an insertion procedure of the tympanostomy tube 50. For example, the tympanostomy tube 50 may be inserted while it is in the first configuration. Once properly positioned, the tympanostomy tube 50 may be heated above its transformation temperature, such as by using a laser, electrocautery, heat probe, or other device, to transform the tympanostomy tube 50 from the first configuration to the second configuration. The tympanostomy tube 50 will remain in its second configuration while residing in the ear 10 (FIG. 1).

According to some embodiments, a laser or heat target grasping tab 68 may optionally be provided. The tab 68 may be designed to absorb heat energy, as a surface separate from the tube ventilation function, and conduct it into the tube foil material. The target may be designed so as to protect the eardrum tissues against damage by direct laser firing. If only the narrow tube was present, then laser firing at the tube may miss the tube or may be larger in diameter than the tube and hit and damage the eardrum. The tab 68 can also be used for grasping during tube insertion.

Figure 5:
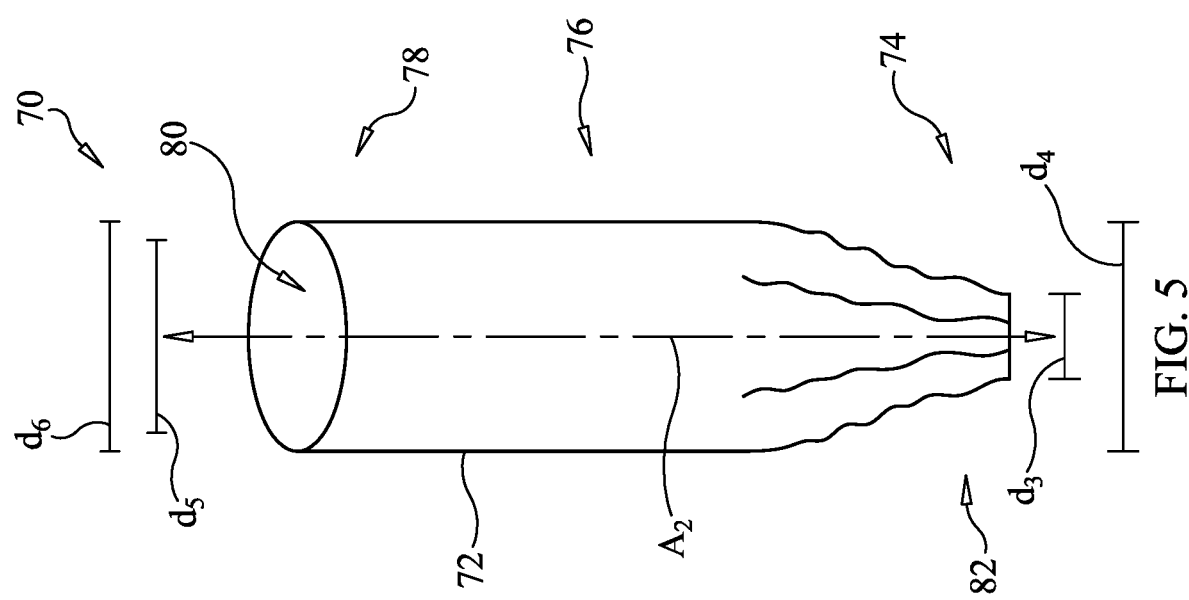
FIG. 5 is a side view of another exemplary embodiment of a tympanostomy tube, shown in a first configuration, according to the present disclosure.

Turning now to FIG. 5, another exemplary embodiment of a tympanostomy tube 70, according to the present disclosure, is shown. The tympanostomy tube 70 generally includes a nitinol body/foil 72 and has a first configuration and a second configuration. The nitinol body/foil 72 may define the body of the tympanostomy tube 70 and may be made from a thin sheet of nickel titanium alloy, also referred to as nitinol, or other shape memory material.

In the first configuration, the nitinol body/foil 72 has a first cylindrical, or other geometric, shape, as shown. The nitinol body/foil 72, according to the first configuration, defines a first end 74, a central region 76, a second end 78, a longitudinal axis $A_2$, and a lumen 80 extending longitudinally through the nitinol body/foil 72. When placed in the ear 10 of FIG. 1, the first end 74 may be positioned in the middle ear portion 14, the central region 76 may be positioned through the tympanic membrane 24, and the second end 78 may be positioned within the outer ear portion 12. The lumen 80, which is substantially parallel to the longitudinal axis $A_2$, provides ventilation of the middle ear portion 14.

The first end 74 may include a tapered tip 82 useful in entering through the tympanic membrane 24 during insertion of the tympanostomy tube 70. The tapered tip 82 may be formed a number of different ways, such as, for example, by pressing or crushing the first end 74. An inner diameter $d_3$ and an outer diameter $d_4$ at the first end 74 may both be smaller than the corresponding inner diameter $d_5$ and outer diameter $d_6$ at the second end 78.

The tympanostomy tube 70 is formed according to the first configuration with the nitinol body/foil 72 at a first temperature. When the tympanostomy tube 70 is heated above its transformation temperature, it will transform according to the second configuration, shown in FIG. 6. According to the second configuration, the nitinol body/foil 72 has a second cylindrical, or other geometric, shape different than the first cylindrical, or other geometric, shape. In particular, the inner diameter $d_3$ and outer diameters $d_4$ at the first end 74 may increase in the second configuration. The nitinol body/foil 72, in the second configuration, may reverse the pressed or crushed first end 74 to open it and create a continuous lumen along axis $A_2$ such that there is little or no circumferential overlap, as shown.

Figure 6:
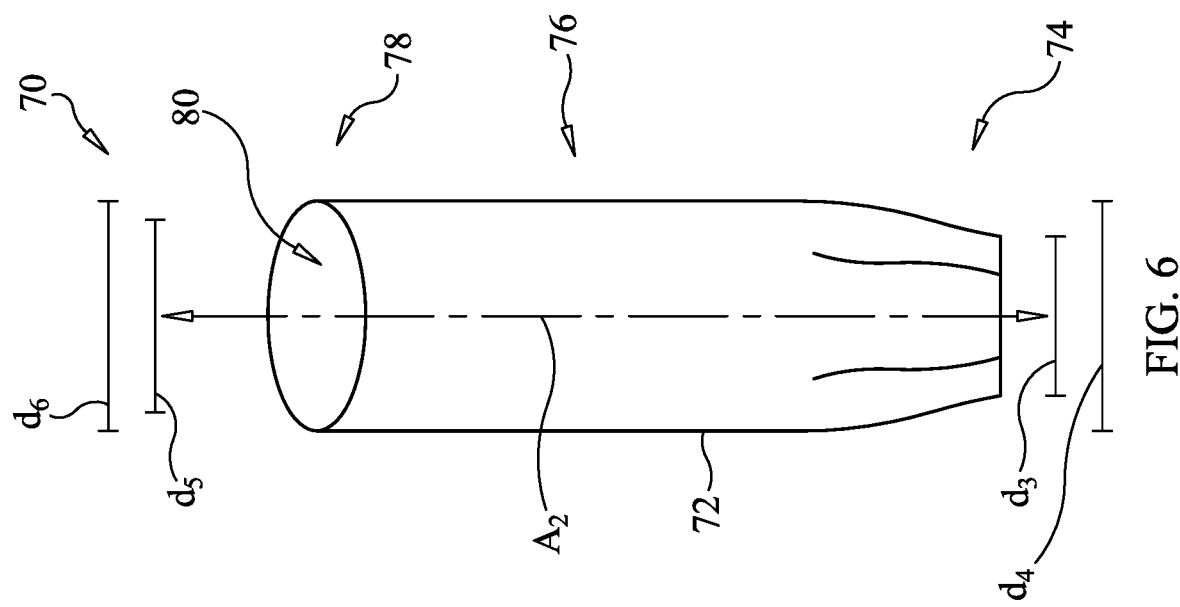
FIG. 6 is a side view of the exemplary tympanostomy tube of FIG. 5, shown in a second configuration, according to the present disclosure.

Transformation of the tympanostomy tube 70 from the first configuration, of FIG. 5, to the second configuration, of FIG. 6, may occur during an insertion procedure of the tympanostomy tube 70. For example, the tympanostomy tube 70 may be inserted while it is in the first configuration. Once properly positioned, the tympanostomy tube 70 may be heated above its transformation temperature, such as by using a laser or other device, to transform the tympanostomy tube 70 from the first configuration to the second configuration. After the procedure, the tympanostomy tube 70 will remain in place in the ear 10 (FIG. 1) according to the second configuration.

Figure 7:
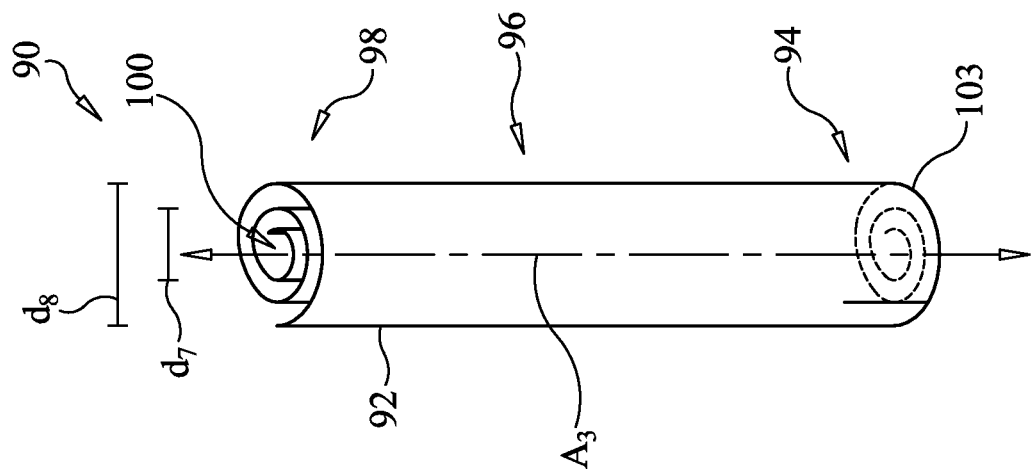
FIG. 7 is a side view of yet another exemplary embodiment of a tympanostomy tube, shown in a first configuration, according to the present disclosure.

Turning now to FIG. 7, another exemplary embodiment of a tympanostomy tube 90, according to the present disclosure, is shown. The tympanostomy tube 90 generally includes a nitinol body/foil 92 and has a first configuration and a second configuration. The nitinol body/foil 92 may define the body of the tympanostomy tube 90 and may be made from a thin sheet of nickel titanium alloy, also referred to as nitinol, or other shape memory material.

Figure 8:
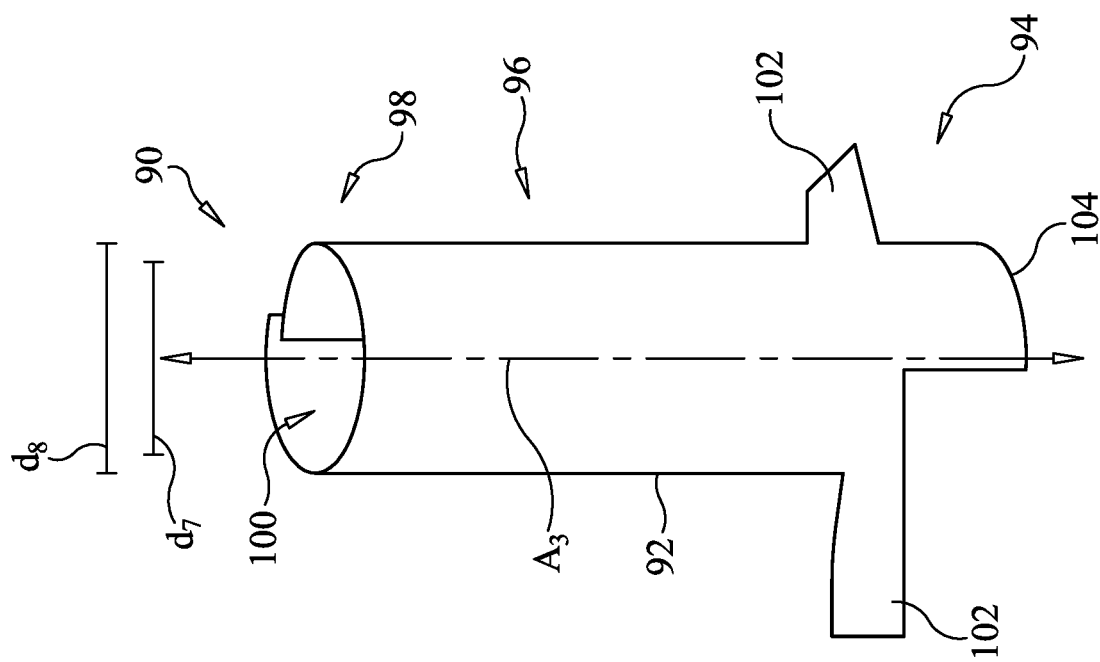
FIG. 8 is a side view of the tympanostomy tube of FIG. 7, shown in a second figuration, according to the present disclosure.

In the first configuration, the nitinol body/foil 92 is scrolled and has a first cylindrical, or other geometric, shape, as shown. The nitinol body/foil 92, according to the first configuration, defines a first end 94, a central region 96, a second end 98, a longitudinal axis $A_3$, and a lumen 100 extending longitudinally through the nitinol body/foil 92. When placed in the ear 10 of FIG. 1, the first end 94 may be positioned in the middle ear portion 14, the central region 96 may be positioned through the tympanic membrane 24, and the second end 98 may be positioned within the outer ear portion 12. The lumen 100, which is substantially parallel to the longitudinal axis $A_3$, provides ventilation of the middle ear portion 14. There are incisions 103 through the second end 98 parallel or spiral to axis $A_3$, which create flaps 102, 104, shown in FIG. 8.

The tympanostomy tube 90 is formed according to the first configuration with the nitinol body/foil 92 at a first temperature. When the tympanostomy tube 90 is heated above its transformation temperature, it will transform according to the second configuration, shown in FIG. 8. According to the second configuration, the nitinol body/foil 92 is un-scrolled and has a second cylindrical, or other geometric, shape different than the first cylindrical, or other geometric, shape. In particular, the inner diameter $d_7$ and the outer diameter $d_8$ may both increase in the second configuration. The nitinol body/foil 92 may be un-scrolled such that there is little or no circumferential overlap, as shown, and the outer diameter $d_5$ be sized to be retain the tympanostomy tube 90 in proper positioning with the ear 10 for at least a first predetermined period of time.

Further, the tympanostomy tube, such as tympanostomy tube 90, may include flaps 102, 104, which may lie parallel to the longitudinal axis $A_3$ in the first configuration, and may move to a position perpendicular to the longitudinal axis $A_3$ in the second configuration. For example, flaps 102 may move to a perpendicular position while flaps 104 may remain parallel to the longitudinal axis $A_3$. Transformation of the tympanostomy tube 90 from the first configuration, of FIG. 7, to the second configuration, of FIG. 8, may occur during an insertion procedure of the tympanostomy tube 90. For example, the tympanostomy tube 90 may be inserted while it is in the first configuration. Once properly positioned, the tympanostomy tube 90 may be heated above its transformation temperature, such as by using a laser or other device, to transform the tympanostomy tube 90 from the first configuration to the second configuration. After insertion, the flaps 102 may function to prevent rejection and extrusion of the tympanostomy tube 90 from the tympanic membrane 24.

Figure 4:
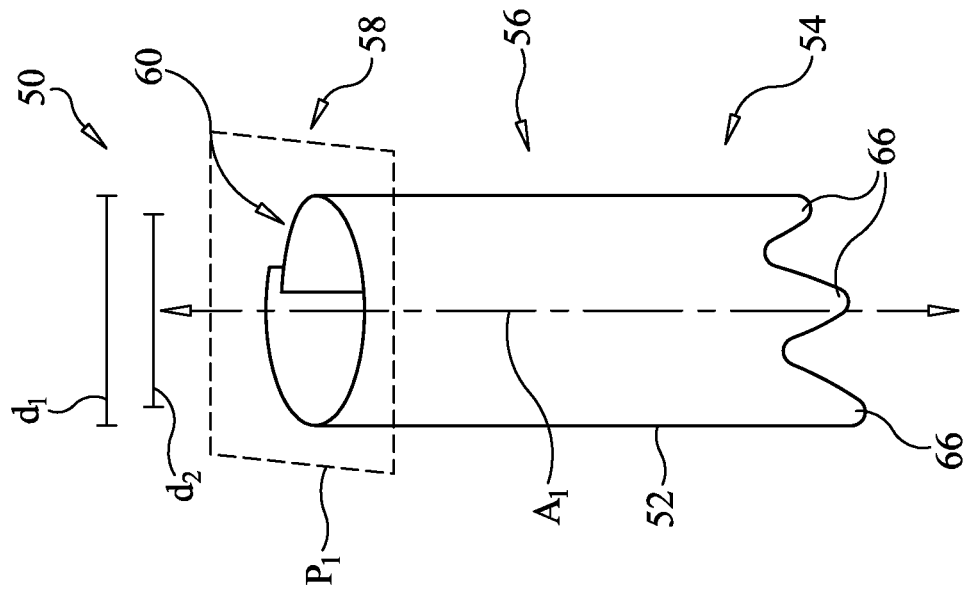
FIG. 4 is a side view of the exemplary tympanostomy tube of FIGS. 2 and 3, shown in a second configuration, according to the present disclosure.
Figure 9:
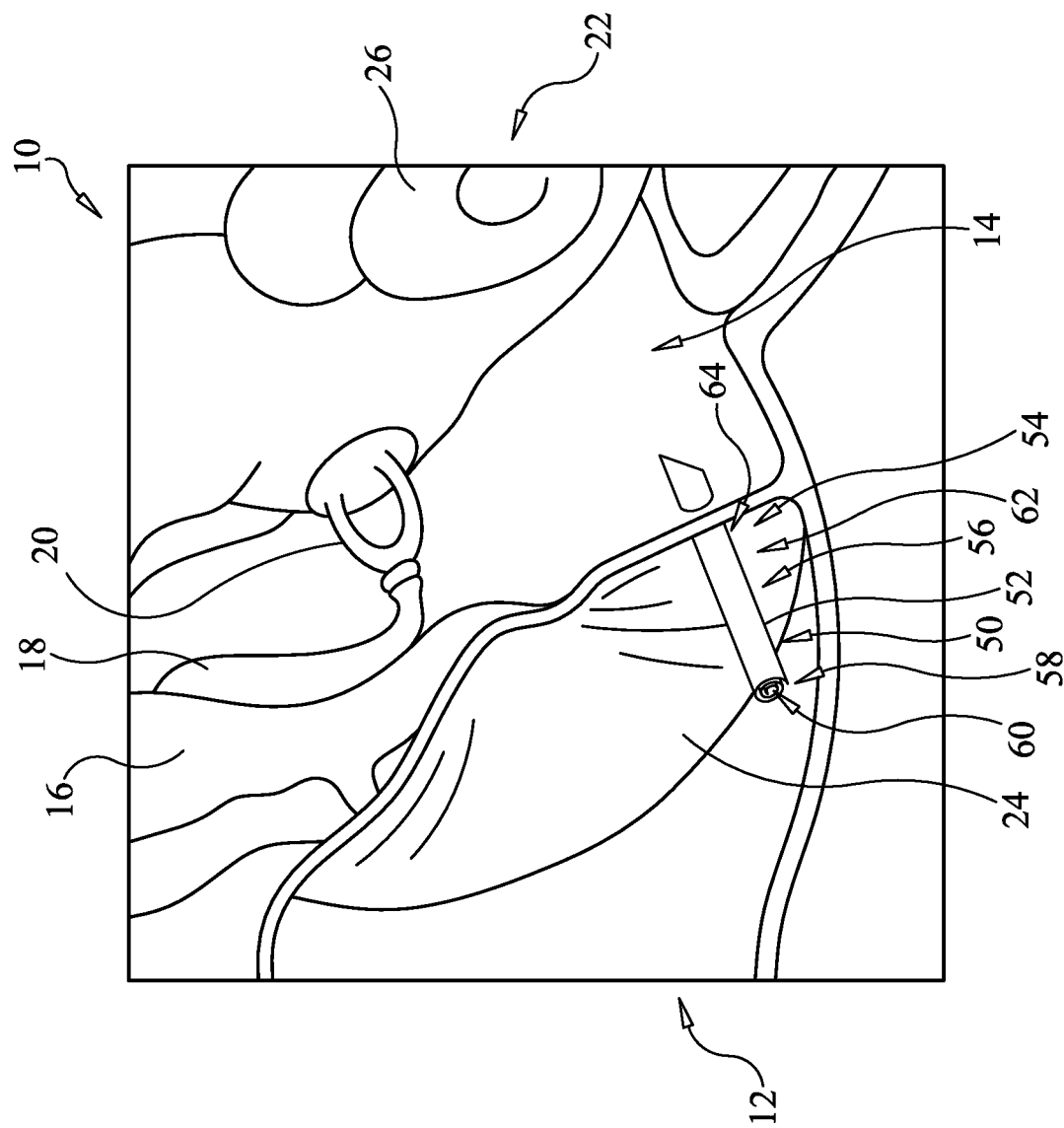
FIG. 9 is a side view of the exemplary tympanostomy tube of FIGS. 2-4, shown at a first stage of a myringotomy procedure, according to the present disclosure.
Figure 10:
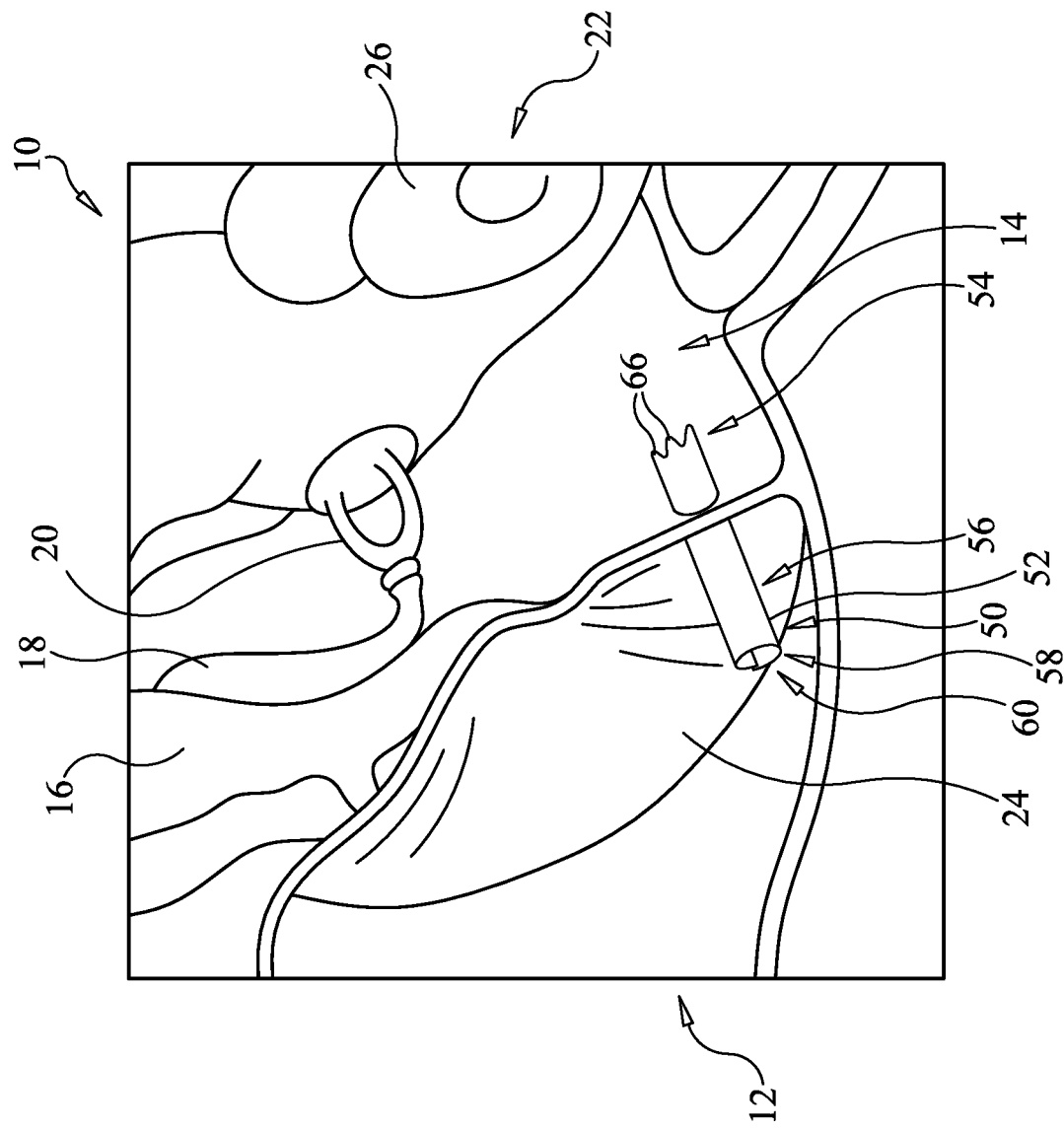
FIG. 10 is a side view of the exemplary tympanostomy tube of FIGS. 2-4, shown at a second stage of a myringotomy procedure, according to the present disclosure.

Turning now to FIGS. 9 and 10, an exemplary procedure for placing the tympanostomy tube 50 of the exemplary embodiment of FIGS. 2-4 is illustrated. The tympanostomy tube 50 may be provided in the first configuration, shown in FIGS. 2 and 3. According to the first configuration, the nitinol body/foil 52 is scrolled and has a first cylindrical, or other geometric, shape defining a first end 54, a central region 56, a second end 58, a longitudinal axis $A_1$, and a lumen 60 extending longitudinally through the nitinol body/foil 52. According to this configuration, the second end 58 may terminate in edges lying in a plane $P_1$ substantially perpendicular to the longitudinal axis $A_1$. The first end 54 may terminate in edges that lie in a different plane $P_2$ that is angled relative to the longitudinal axis $A_1$, thus defining a scrolled bevel 62. The first end 54, or beveled scroll 62 thereof, may be useful in piercing or cutting the tympanic membrane 24 during insertion of the tympanostomy tube 50.

After the first end 54 of the tympanostomy tube 50 is used to pierce the tympanic membrane 24, the central region 56 of the tympanostomy tube 50 may thereafter be passed into or through the tympanic membrane 24. When placed in the ear 10, the first end 54 may be positioned in the middle ear portion 14, the central region 56 may be positioned through the tympanic membrane 24, and the second end 58 may be positioned within the outer ear portion 12. The lumen 60, which is substantially parallel to the longitudinal axis $A_1$, provides ventilation of the middle ear portion 14.

Once properly positioned, the tympanostomy tube 50 may be heated above its transformation temperature, such as by using a laser or other device, to transform the tympanostomy tube 50 from the first configuration of FIGS. 2 and 3 to the second configuration of FIG. 4. According to the second configuration, the nitinol body/foil 52 is un-scrolled and has a second cylindrical, or other geometric, shape different than the first cylindrical, or geometric, shape. In particular, the outer diameter $d_1$ and the inner diameter $d_2$ may both increase in the second configuration.

Figure 12:
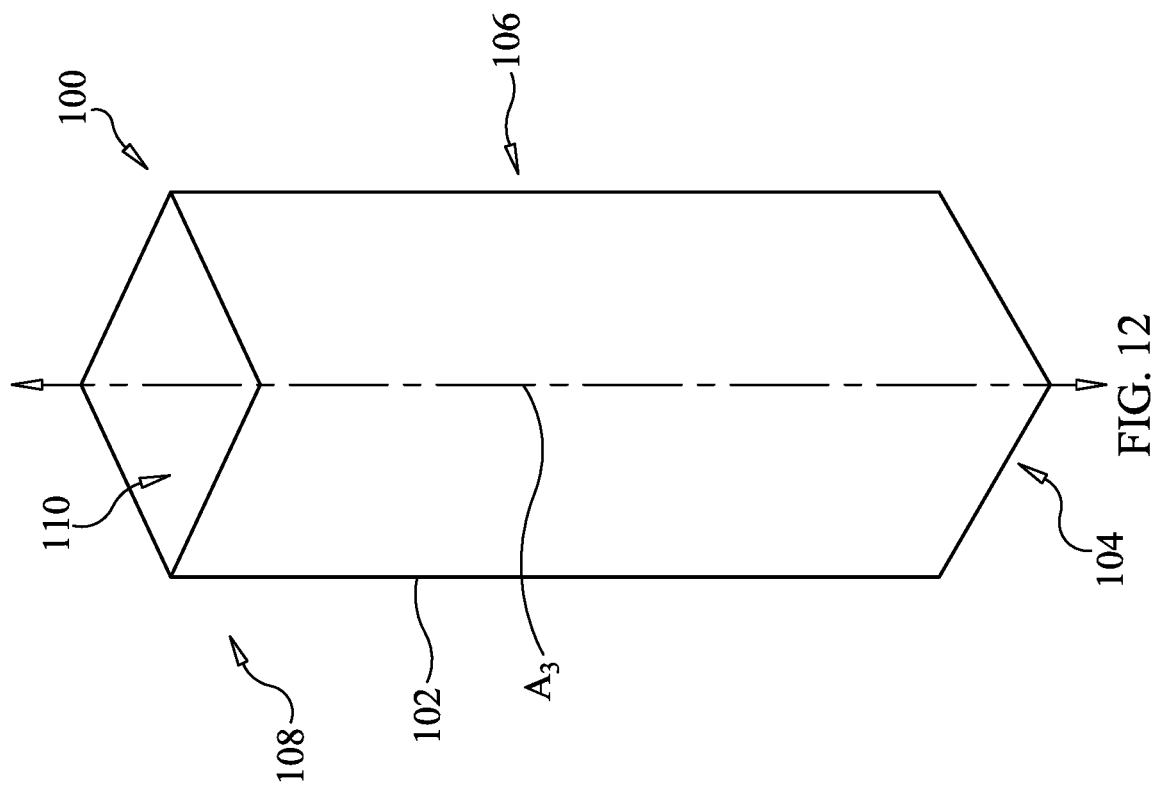
FIG. 12 is a side view of the tympanostomy tube of FIG. 11, shown in a second configuration, according to the present disclosure.
Figure 11:
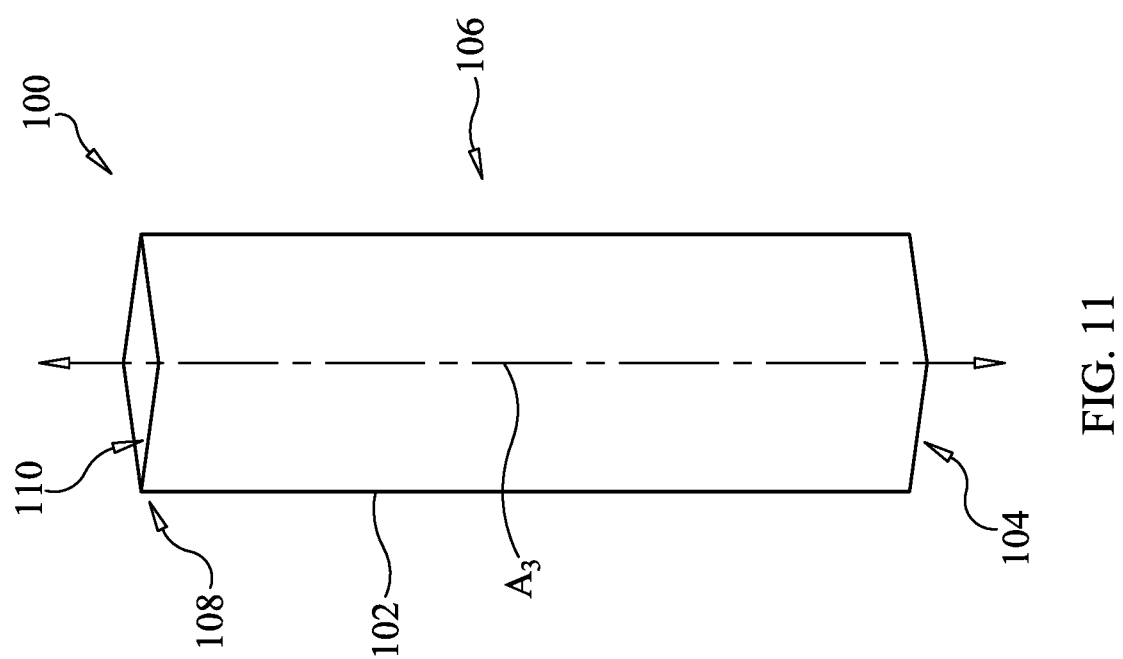
FIG. 11 is a side view of yet another exemplary embodiment of a tympanostomy tube, shown in a first configuration, according to the present disclosure.

Additional alternative embodiments may be shown in FIGS. 11-18. In particular, in FIGS. 11 and 12, a tympanostomy tube 100 may include a nitinol body/foil 102 and has a first configuration and a second configuration. The nitinol body/foil 102 may define the body of the tympanostomy tube 100 and may be made from a thin sheet of nickel titanium alloy, also referred to as nitinol, or other shape memory material. In the first configuration, the nitinol body/foil 102 is flattened and has a first geometric shape, as shown. The nitinol body/foil 102, according to the first configuration, defines a first end 104, a central region 106, a second end 108, a longitudinal axis $A_3$, and a lumen 110 extending longitudinally through the nitinol body/foil 102. When placed in the ear 10 of FIG. 1, the first end 104 may be positioned in the middle ear portion 14, the central region 106 may be positioned through the tympanic membrane 24, and the second end 108 may be positioned within the outer ear portion 12. Once activated above its transformation temperature it will take on the new second configuration of FIG. 12. The expanded lumen 110, which is substantially parallel to the longitudinal axis $A_3$, provides ventilation of the middle ear portion 14. The second, or expanded, configuration of the tympanostomy tube 100 is shown in FIG. 12.

Figure 14:
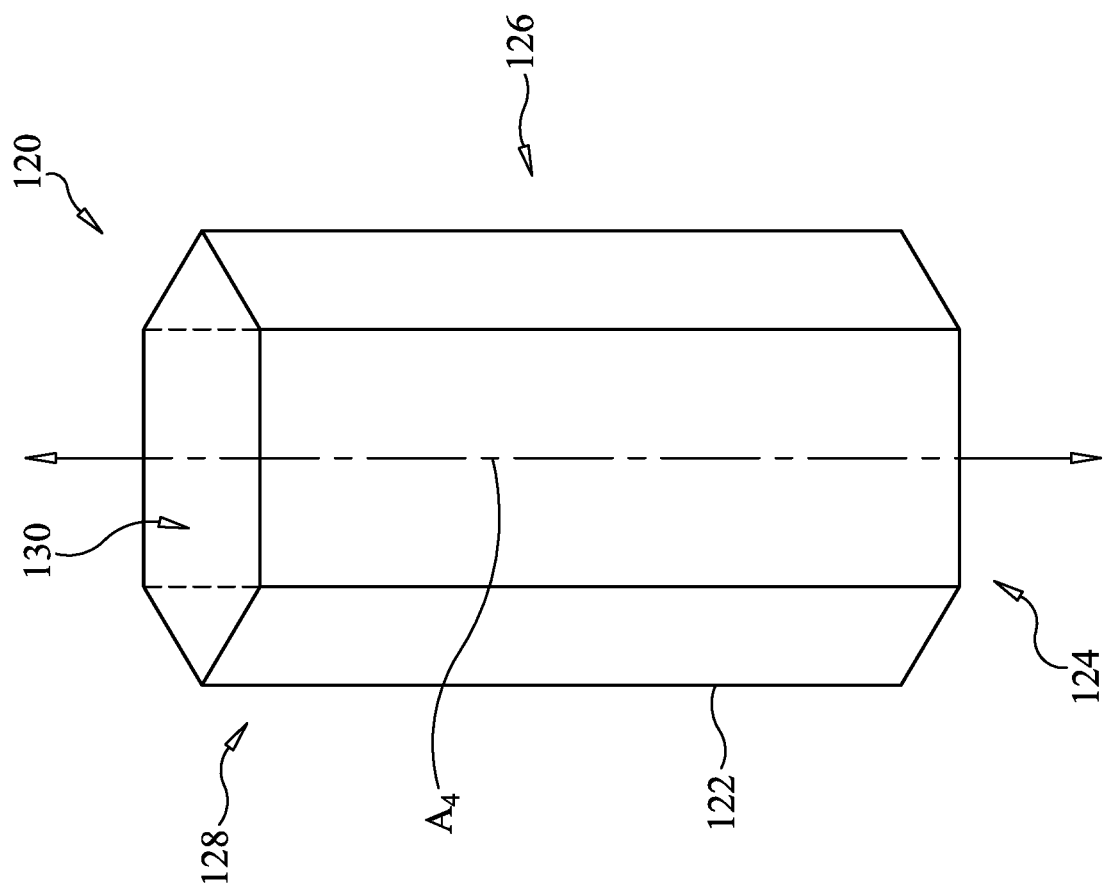
FIG. 14 is a side view of the tympanostomy tube of FIG. 13, shown in a second configuration, according to the present disclosure.
Figure 13:
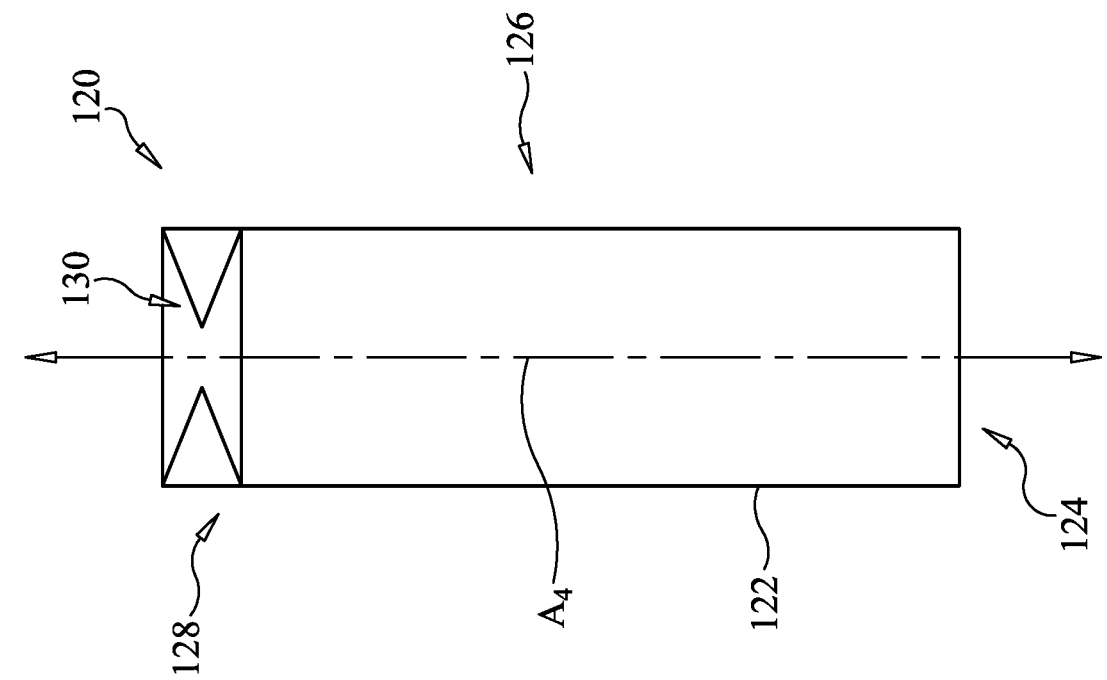
FIG. 13 is a side view of yet another exemplary embodiment of a tympanostomy tub, show in a first configuration, according to the present disclosure.

Referring to FIGS. 13 and 14, a tympanostomy tube 120 may include a nitinol body/foil 122 and has a first configuration and a second configuration. The nitinol body/foil 122 may define the body of the tympanostomy tube 120 and may be made from a thin sheet of nickel titanium alloy, also referred to as nitinol, or other shape memory material. In the first configuration, the nitinol body/foil 122 is folded and has a first geometric shape, as shown. The nitinol body/foil 122, according to the first configuration, defines a first end 124, a central region 126, a second end 128, at longitudinal axis $A_4$, and a lumen 130 extending longitudinally through the nitinol body/foil 122. When placed in the ear 10 of FIG. 1, the first end 124 may be positioned in the middle ear portion 14, the central region 126 may be positioned through the tympanic membrane 24, and the second end 128 may be positioned within the outer ear portion 12. After placement, the first configuration of FIG. 13 is activated by heat to change into the second configuration of FIG. 14. The lumen 130, which is substantially parallel to the longitudinal axis $A_4$, has been enlarged and provides ventilation of the middle ear portion 14 in the second configuration.

Referring to FIGS. 15 and 16, a tympanostomy tube 140 may include a nitinol body/foil 142 and has a first configuration and a second configuration. The nitinol body/foil 142 may define the body of the tympanostomy tube 140 and may be made from a thin sheet of nickel titanium alloy, also referred to as nitinol, or other shape memory material. In the first configuration, the nitinol body/foil 142 is plicated and has a first geometric shape, as shown. The nitinol body/foil 142, according to the first configuration, defines a first end 144, a central region 146, a second end 148, at longitudinal axis $A_5$, and a lumen 150 extending longitudinally through the nitinol body/foil 142. When placed in the ear 10 of FIG. 1, the first end 144 may be positioned in the middle ear portion 14, the central region 146 may be positioned through the tympanic membrane 24, and the second end 148 may be positioned within the outer ear portion 12. The lumen 150, which is substantially parallel to the longitudinal axis $A_5$, when expanded by heating into the second configuration of FIG. 16, provides ventilation of the middle ear portion 14.

Figure 18:
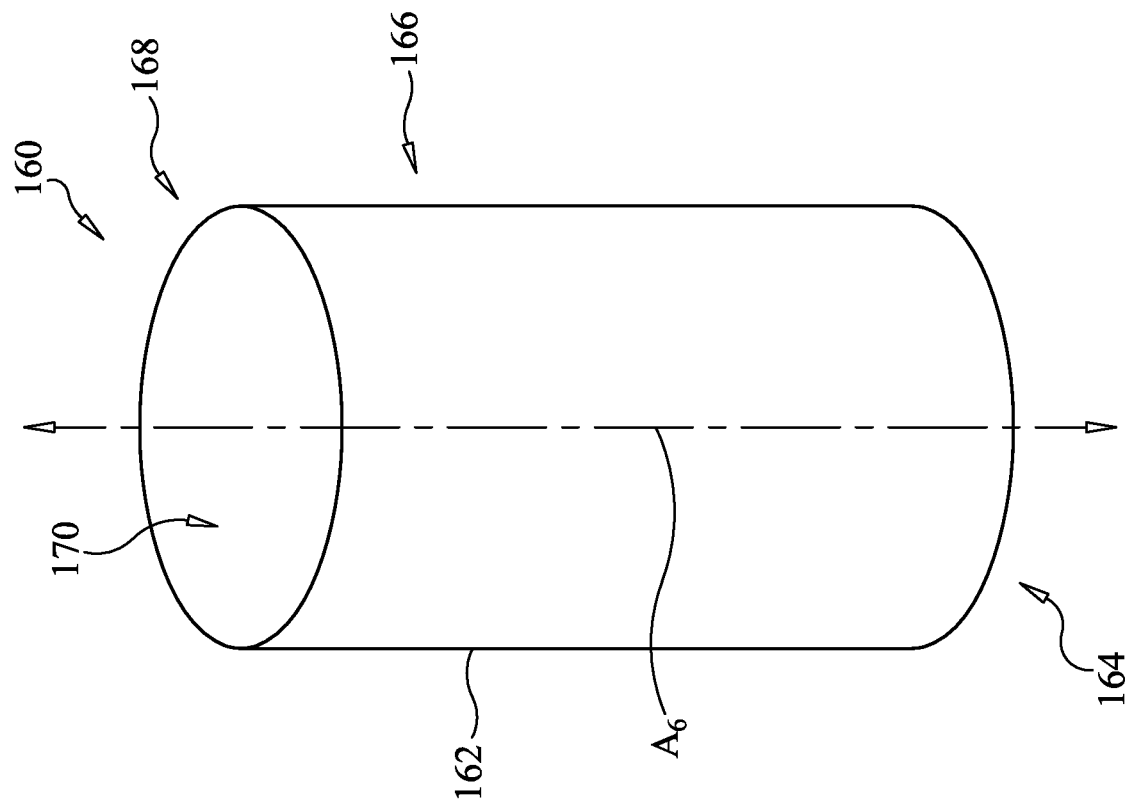
FIG. 18 is a side view of the tympanostomy tube of FIG. 17, shown in a second configuration, according to the present disclosure.
Figure 17:
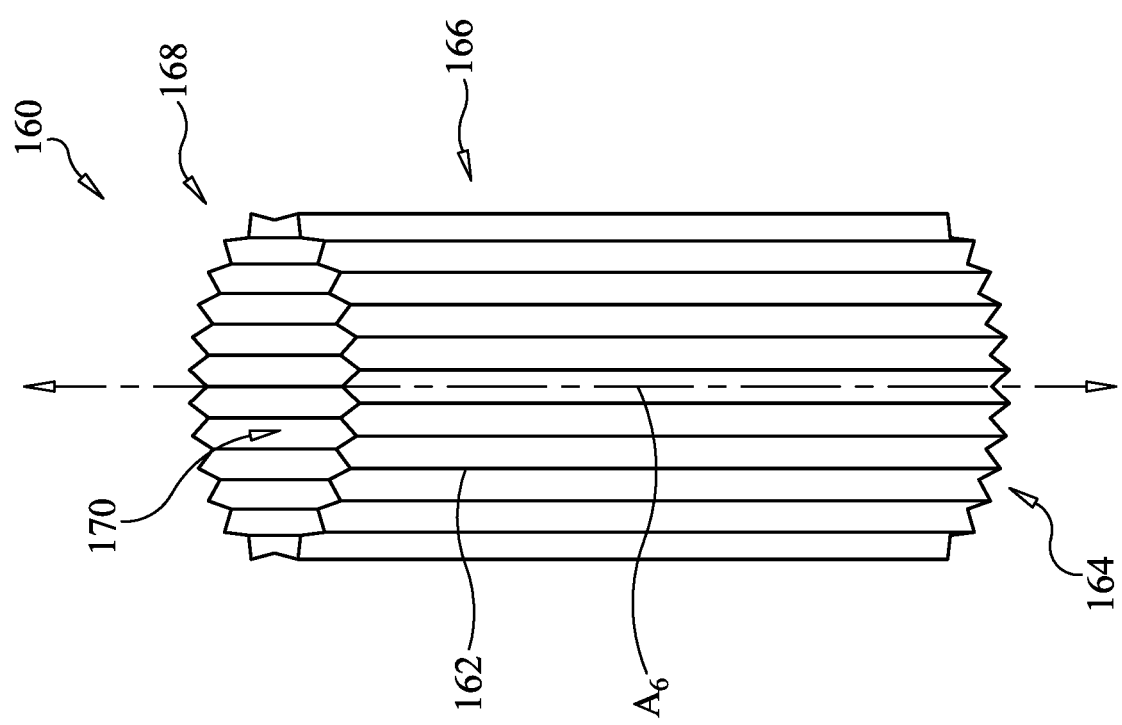
FIG. 17 is a side view of yet another exemplary embodiment of a tympanostomy tub, show in a first configuration, according to the present disclosure.

Referring to FIGS. 17 and 18, a tympanostomy tube 160 may include a nitinol body/foil 162 and has a first configuration and a second configuration. The nitinol body/foil 162 may define the body of the tympanostomy tube 160 and may be made from a thin sheet of nickel titanium alloy, also referred to as nitinol, or other shape memory material. In the first configuration, the nitinol body/foil 162 is imbricated and has a first geometric shape, as shown. The nitinol body/foil 162, according to the first compressed accordion-like configuration, defines a first end 164, a central region 166, a second end 168, at longitudinal axis $A_6$, and a lumen 170 extending longitudinally through the nitinol body/foil 162. When placed in the ear 10 of FIG. 1, the first end 164 may be positioned in the middle ear portion 14, the central region 166 may be positioned through the tympanic membrane 24, and the second end 168 may be positioned within the outer ear portion 12. The lumen 170, which is substantially parallel to the longitudinal axis $A_6$, provides ventilation of the middle ear portion 14 when it has been expanded into the second configuration of FIG. 18.

The tympanostomy tube 160 is formed according to the first configuration with the nitinol body/foil 162 at a first temperature. When the tympanostomy tube 160 is heated above its transformation temperature, it will transform according to the second configuration, shown in FIG. 18. According to the second configuration, the nitinol body/foil 162 is expanded in an accordion-like manner losing the imbrications and changing into the second cylindrical, or geometric, shape different than the first cylindrical, or geometric, shape. The nitinol body/foil 162 may be expanded such that there is little or no circumferential imbrication or overlap, as shown, and the tympanostomy tube 160 will remain in place in the ear 10 for a medically useful period of time.

The tympanostomy tubes disclosed herein may eliminate the step of using a myringotomy knife to make an incision in the tympanic membrane during a procedure to insert the tympanostomy tube. Respective first ends of the tympanostomy tubes may be suitably configured and shaped to enter through the tympanic membrane during the insertion. As such, the number of procedure steps required, and the associated cost, is reduced. Although at least eight embodiments of tympanostomy tubes are disclosed, numerous alternative embodiments are contemplated without deviating from the scope of the present disclosure.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure, and the appended claims.

What is claimed is:
1. A tympanostomy tube, comprising:
a nitinol body having a substantially cylindrical shape, wherein the nitinol body includes a first end, a central region, a second end, a longitudinal axis, and a lumen, and wherein the nitinol body is configured to transition between a first configuration and a second configuration;
wherein the nitinol body has a first diameter in the first configuration, wherein the first end defines a cutting member in the first configuration, and wherein the cutting member is configured to incise the tympanic membrane during insertino of the tympanostomy tube in the tympanic membrane;
a heat target grasping tab located at the second end of the nitinol body, wherein the heat target grasping tab partially extends about a circumference of the nitinol body, wherein the heat target grasping tab extends radially outward from the nitinol body in the first configuration, and wherein the heat target grasping tab is configured to absorb heat energy and conduct the heat energy into the nitinol body; and
wherein the nitinol body is configured to transition from the first configuration to the second configuration in response to the heat energy, wherein the nitinol body has a second diameter in the second configuration, and wherein the second diameter is larger than the first diameter.

2. The tympanostomy tube of claim 1, wherein, in the first configuration, the nitinol body is scrolled, and wherein, in the second configuration, the nitinol body is un-scrolled.

3. The tympanostomy tube of claim 2, wherein, in the first configuration, the cutting member is a beveled scroll.

4. The tympanostomy tube of claim 1, further including incisions through the second end parallel to the longitudinal axis defining tabs extending radially in the second configuration.

5. The tympanostomy tube of claim 1, wherein, in the first configuration, the nitinol body is flattened, and wherein, in the second configuration, the nitinol body is un-flattened.

6. The tympanostomy tube of claim 1, wherein, in the first configuration, the nitinol body is folded, and wherein, in the second configuration, the nitinol body is un-folded.

7. The tympanostomy tube of claim 1, wherein, in the first configuration, the nitinol body is plicated, and wherein, in the second configuration, the nitinol body is un-plicated.

8. The tympanostomy tube of claim 1, wherein, in the first configuration, the nitinol body has an imbricated accordion-like configuration, and wherein, in the second configuration, the nitinol body has a circular configuration.

9. A tympanostomy tube, comprising:
a nitinol body having a first end, a central region, a second end, and a lumen;
wherein the nitinol body is configured to transform from a first configuration to a second expanded configuration;
wherein in the first configuration, the first end defines a cutting member configured to incise the tympanic membrane during insertion of the tympanostomy tube in the tympanic membrane;
a heat target grasping tab located at the second end of the nitinol body, wherein the heat target grasping tab extends radially outward from the nitinol body in the first configuration, wherein the heat target grasping tab partially extends about a circumference of the nitinol body, and wherein the heat target grasping tab is configured to absorb heat energy and transfer the heat energy to the nitinol body; and
wherein in response to the heat energy transferred to the nitinol body, the nitinol body transforms from the first configuration to the second expanded configuration.

10. The tympanostomy tube of claim 9, wherein nitinol body-is scrolled in the first configuration, and the nitinol body is un-scrolled in the second expanded configuration.

11. The tympanostomy tube of claim 10, wherein a beveled scroll defines the cutting member.

12. The tympanostomy tube of claim 9, wherein the cutting member is a tapered tip.

13. The tympanostomy tube of claim 9, further including incisions through the second end parallel to a longitudinal axis defining tabs, wherein the tabs extend radially in the second expanded configuration.

14. The tympanostomy tube of claim 9, wherein the nitinol body is flattened in the first configuration, and wherein the nitinol body is un-flattened in the second expanded configuration.

15. The tympanostomy tube of claim 9, wherein the nitinol body is folded in the first configuration, and wherein the nitinol body is un-folded in the second expanded configuration.

16. The tympanostomy tube of claim 9, wherein the nitinol body is plicated in the first configuration, and wherein the nitinol body is un-plicated in the second expanded configuration.

17. The tympanostomy tube of claim 9, wherein the nitinol body transforms from an imbricated accordion-like shape in the first configuration to a circular shape in the second configuration.

* * * * *